United States Patent [19]
Genders et al.

[11] Patent Number: 6,004,445
[45] Date of Patent: Dec. 21, 1999

[54] ELECTROCHEMICAL METHODS FOR RECOVERY OF ASCORBIC ACID

[75] Inventors: J. David Genders, Marilla; Dan M. Hartsough, Clarence, both of N.Y.

[73] Assignee: Electrosynthesis Company, Inc., Lancaster, N.Y.

[21] Appl. No.: 09/108,144

[22] Filed: Jun. 30, 1998

Related U.S. Application Data

[60] Provisional application No. 60/051,199, Jun. 30, 1997.

[51] Int. Cl.$^6$ .................................................. B01D 61/44
[52] U.S. Cl. ..................... 204/537; 204/537; 204/538; 204/541; 205/427; 205/455
[58] Field of Search .................................. 205/427, 455; 204/537, 538, 541

[56] References Cited

U.S. PATENT DOCUMENTS

| | | | |
|---|---|---|---|
| 3,968,017 | 7/1976 | Canata et al. | 204/541 |
| 4,767,870 | 8/1988 | Fujiwara et al. | 549/315 |
| 4,781,809 | 11/1988 | Falcone et al. | 204/182.4 |
| 4,882,277 | 11/1989 | Czytko et al. | 435/136 |
| 5,034,105 | 7/1991 | Berglund et al. | 204/182.4 |
| 5,049,250 | 9/1991 | Chlanda | 204/182.4 |
| 5,198,086 | 3/1993 | Chlanda et al. | 204/182.4 |
| 5,202,445 | 4/1993 | Dobler et al. | 549/315 |
| 5,681,728 | 10/1997 | Miao | 204/530 X |
| 5,702,579 | 12/1997 | Veits | 204/530 X |

*Primary Examiner*—Arun S. Phasge
*Attorney, Agent, or Firm*—Marianne Fuierer; Howard M. Ellis

[57] ABSTRACT

The present invention relates to electrochemical methods for the recovery of ascorbic acid from an ascorbate salt without the co-generation of a waste salt stream and while maintaining high conductivity of the electrochemical cell thereby providing for quantitative conversion of the salts to ascorbic in both batch and continuous mode processes. In one embodiment the feed stream comprising an ascorbate salt is dissociated under the influence of an electric field and subjected to water splitting electrodialysis. The ascorbate ion combines with a proton and the salt cation combines with a hydroxyl ion to form ascorbic acid and base, respectively. The feed stream further comprises an inorganic salt which maintains high conductivity in the cell, facilitates quantitative conversion of ascorbate salts to ascorbic acid in both batch and continuous mode processes, and promotes precipitation and crystallization of ascorbic acid as a fine powder. Electrochemical cells useful in the methods include arrangements with a combination of at least one cation membrane, and at least one bipolar membrane in combination with at least one cation membrane.

23 Claims, 5 Drawing Sheets

ELECTROCHEMICAL METHODS FOR RECOVERY OF ASCORBIC ACID

CROSS REFERENCE TO RELATED APPLICATION

This application claims the benefit of U.S. Provisional application Ser. No 60/051,199 filed on Jun. 30, 1997.

TECHNICAL FIELD

The present invention relates to producing ascorbic acid and more particularly to novel electrochemical methods for generating ascorbic acid from ascorbate salts while avoiding the formation of a waste salt stream, providing improved conductivity and converting ascorbate salts to ascorbic acid in a continuous process.

BACKGROUND OF THE INVENTION

Vitamin C is synthesized in plants and most higher animals from D-glucose. However, humans have a genetic defect that prevents the synthesizing of vitamin C. In this regard, humans must consume the required vitamin C in their diets or by supplementation. Because of the recognized need and demand for vitamin C, several different methods for synthesizing it are currently utilized, including the Reichstein process. The starting material for the Reichstein process is glucose, which is converted in several steps to 2-Keto-L-gulonic acid (KLG). KLG is esterified with methanol and acid to form the KLG methyl ester, which is then treated with sodium methoxide in methanol to give sodium ascorbate. Sodium ascorbate is then acidified with sulfuric or hydrochloric acid to give the ascorbic acid product plus an equimolar quantity of an unwanted waste salt.

To eliminate the need of introducing an acid into the ascorbate salt solution which forms a waste salt stream, U.S. Pat. No. 5,702,579 discloses a method of protonating ascorbate salts via electrodialysis using bipolar membranes and monopolar membranes. In this patent publication, the feed stream introduced into the electrochemical cell is limited to an ascorbate salt solution. By limiting the feed stream to just an ascorbate salt solution the conductivity of the electrochemical cell constantly decreases. As such, cell voltage during constant current operation will constantly increase to compensate for the decreased conductivity thereby increasing the overall cost of converting the ascorbate salt to ascorbic acid. Also, continuous conversion of ascorbate salts to ascorbic acid is not efficiently achieved because the presence of increased amounts of ascorbate salts in solution increases the solubility of ascorbic acid thereby rendering it less likely to precipitate out of solution and form fine powder crystals on a continuous basis.

Accordingly, simple electrochemical methods are needed which convert ascorbate salt to ascorbic acid without producing a stream of waste salt, which offer improved conductivity of the feed solution thereby reducing high voltage requirements, and which offer the ability to operate at quantitative conversion of ascorbate salt to ascorbic acid in both batch and continuous mode.

SUMMARY OF THE INVENTION

It is the principal object of this invention to provide novel electrochemical methods for the recovery of ascorbic acid from sodium ascorbate or other ascorbate salts without the co-generation of a waste salt stream and while maintaining high conductivity of the cell thereby providing for quantitative conversion of the salts to the acid in both batch and continuous mode processes. Additionally, the present invention produces useful by-products such as the hydroxide, carbonate, or bicarbonate of the ascorbate cation when the process is practiced in aqueous solution, or the methoxide salt of the cation when practiced in methanol with bipolar membranes. Bicarbonate or methoxide co-products can be used earlier in the ascorbic acid synthesis to carry out the lactonization of the KLG methyl ester forming the ascorbate salt. If hydroxide is produced as the co-product, it can either be used for in-house neutralizations or sold externally.

This object is achieved principally through an electrochemical process for producing ascorbic acid and a base, such as caustic soda or bicarbonate comprising the following steps:

a) providing an electrochemical cell comprising an anode in an anolyte compartment, a cathode in a catholyte compartment, and a central compartment disposed between the anolyte and catholyte compartments, the central compartment separated from the anolyte and catholyte compartments by a first and second cation exchange membrane;

b) introducing into the central compartment a feed solution comprising an ascorbate salt and an inorganic salt;

c) introducing into the anolyte compartment an anolyte comprising an acid;

d) introducing into the catholyte compartment a catholyte comprising a base;

e) applying a sufficient voltage across the anode and cathode to convert the ascorbate salt into an ascorbate ion and salt cation, and to form protons at the anode and hydroxyl ions at the cathode wherein the protons migrate through the first cation exchange membrane to the central compartment to combine with an ascorbate ion to form ascorbic acid and the salt cation migrates through the second cation exchange membrane into the catholyte compartment to combine with the hydroxyl ion to form the co-product base.

A further embodiment of the present invention involves an electrochemical method for the production of ascorbic acid and a useful co-product base comprising the following steps:

a) providing an electrochemical cell comprising an anode, the anode rinsed with an anolyte stream, a cathode, the cathode rinsed with a catholyte stream, and an electrodialysis cell stack disposed between the anode and the cathode. The electrodialysis cell stack comprises at least one feed compartment and at least one base compartment and alternating bipolar and cation exchange membranes disposed between the feed and base compartments;

b) introducing into the feed compartment a feed solution comprising an ascorbate salt and an inorganic salt;

c) introducing into the base compartment a base electrolyte comprising a base; and d) applying a sufficient voltage across the anode and cathode to convert the ascorbate salt into an ascorbate ion and salt cation, and to form protons and hydroxyl ions at the bipolar membrane, wherein the protons migrate to the feed compartment and the hydroxyl ions migrate to the base compartment. The protons in the feed compartment combine with the ascorbate ion to form ascorbic acid and a displaced salt cation. The displaced salt cation migrates through the cation exchange membrane into the base compartment to combine with the hydroxyl ion to form the co-product base. The useful co-product base may be the same base as introduced into the base compartment, such as sodium hydroxide.

It is yet a further object of this invention to provide a method to produce ascorbic acid and a useful co-product base in a two compartment electrochemical cell with a gas diffusion anode comprising the following steps:

a) providing an electrochemical cell comprising a gas diffusion anode in an anolyte compartment, a cathode in a catholyte compartment, and a cation exchange membrane disposed between the anolyte and catholyte compartments;

b) introducing into the anolyte compartment an anolyte comprising an ascorbate salt and an inorganic salt;

c) introducing into the catholyte compartment a catholyte;

d) introducing into the gas diffusion anode a source of hydrogen gas; and e) applying a sufficient voltage across the anode and cathode to convert the ascorbate salt into an ascorbate ion and salt cation, and to form protons at the anode and hydroxyl ions at the cathode wherein the protons, in the anolyte compartment, combine with the ascorbate ion, to form ascorbic acid and a displaced salt cation. The displaced salt cation migrates through the cation exchange membrane into the catholyte compartment to combine with the hydroxyl ion to form a useful co-product base.

Ascorbic acid is produced from ascorbate salts in these embodiments without the co-generation of an unwanted waste salt stream. These processes may be operated in a continuous mode such that the concentration of ascorbic acid exceeds its solubility in the feed solution and precipitates in a crystallizer separate from the electrochemical cell. Thus production and purification of the ascorbic acid are accomplished in one step. Any metal ascorbate dissolved in a polar solvent selected from a group consisting of water, methanol, or any short chain alcohol may be used as the feed electrolyte. If a methanol system is used, the ascorbate salt will only be slightly soluble but the ascorbic acid product will be more stable.

In order to improve the conductivity of the feed electrolyte solution and hence reduce the cell voltage, an inorganic salt is added to the feed electrolyte solution stream. Any inorganic salt that will improve conductivity of the cell may be used, including, but not limited to an alkali metal sulfate, bisulfate, chloride, phosphate and a mixture thereof. Preferably, sodium sulfate is used in the present invention.

Alternatively, a stable cation exchange resin may be added to the feed solution to provide enhanced conductivity.

It is a further object of the invention to conduct a useful process at the bipolar membrane simultaneous to forming ascorbic acid in the feed compartment. The formation of hydroxide at the bipolar membrane from the dissociation of water allows the formation of useful co-products such as sodium hydroxide or sodium bicarbonate or carbonate. If methanol is the solvent employed, then methoxide may be formed at the bipolar membrane to form sodium methoxide in solution. If bicarbonate or carbonate is the desired catholyte co-product, gaseous carbon dioxide is introduced into the catholyte compartment at a rate sufficient to react with the caustic being formed and to produce the bicarbonate or carbonate salt of the alkali metal cation.

The following sections of drawings and examples further explain these novel methods for the electrochemical formation of ascorbic acid from sodium ascorbate.

DESCRIPTION OF THE PREFERRED EMBODIMENTS

Figure 1:
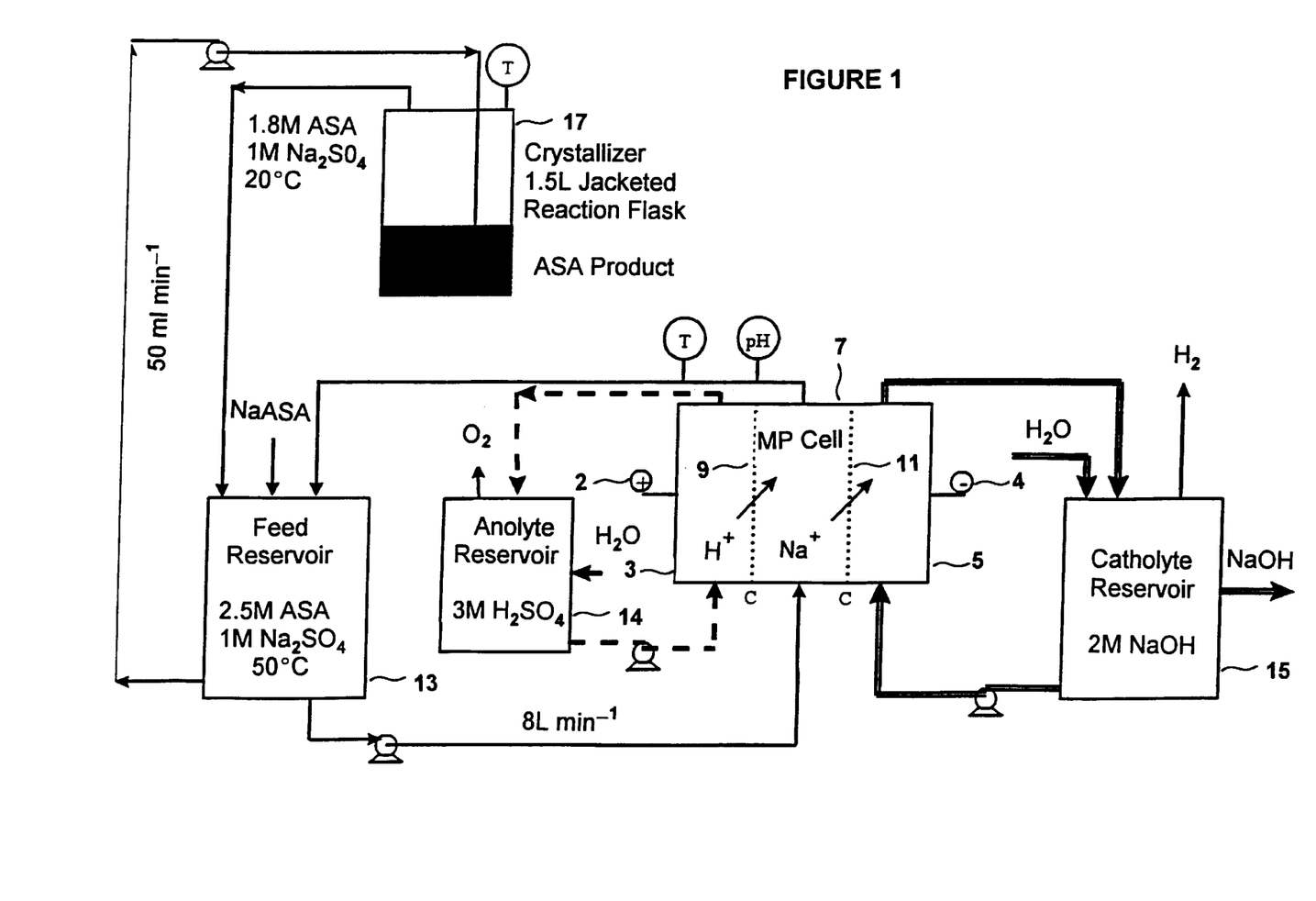
FIG. 1: Diagrammatic View of a Setup for Production of Ascorbic Acid from Sodium Ascorbate in a 3-Compartment Electrochemical Cell

FIG. 1 is a diagrammatic view of a setup for production of ascorbic acid from sodium ascorbate in a three compartment electrochemical cell. The components of a three compartment cell include an anode 2 in an anolyte compartment 3, a cathode 4 in a catholyte compartment 5, a central compartment 7 between the anolyte compartment 3 and catholyte compartment 5. The anode 2 must be stable to the electrolysis conditions and may include carbons, noble metals or alloys of Pt, Pd, Ir, Au, Ru, etc., noble metals or alloys deposited on a valve metal including Ti or Ta. The cathode 4 must be stable and may include carbons, noble metals and alloys, nickel, and steels.

Introduced into the central compartment 7 is a feed electrolyte solution passing from a feed reservoir 13. The feed solution comprises an ascorbate salt. A wide variety of different ascorbate salts well known in the art may be used. Representative examples of useful ascorbate salts include, alkali metal salts, such as sodium, potassium, ammonium salts, and preferably sodium ascorbate. The feed electrolyte may be dissolved in any suitable polar solvent. Useful solvents include, but are not limited to water, methanol, short chain alcohols or a mixture thereof. The feed electrolyte solution of the present invention for use during a continuous mode process contains a sufficient amount of ascorbate salt to replace that which is consumed during the salt splitting electrolysis. In a batch mode process the concentration of ascorbate salt in the feed solution will depend on the polar solvent, temperature and cation used in the process. In general, if the solvent of choice is water then the concentration of ascorbate salt is from about 30 to 70 percent by weight of solution. When methanol is the chosen solvent then the concentration of ascorbate salt is usually less than one (1) percent by weight of solution.

The feed electrolyte solution also contains a sufficient amount of an inorganic salt to improve the conductivity of the solution. Examples of such salts could include alkali metal sulfates, bisulfates, chloride, and phosphates, and preferably sodium sulfate. The inorganic salt by improving the conductivity of the solution decreases the cell voltage requirements of the system and also facilitates higher ascorbate conversion. Without the presence of an inorganic salt the conversion of ascorbate to ascorbic acid is limited by the concentration of free cation in solution. With an inorganic salt present, such as sodium sulfate, this limitation is removed because a large excess of free cation is added to the system which improves the conductivity of the feed stream. This addition allows high current densities to be used even at essentially 100% conversion of ascorbate to ascorbic acid.

It has been found that sodium ascorbate in solution has a solubilizing effect on ascorbic acid which reduces crystallization of the preferred product. Therefore, another advantage of running the process without the need to add additional ascorbate salts to maintain conductivity in the solution is higher recovery of ascorbic acid in a continuous crystallization process. Also, the crystallized ascorbic acid product will not be contaminated by sodium ascorbate thereby providing ascorbic acid product as fine powder crystals.

Additionally, as a result of the improved conductivity of the feed solution, lower cell voltage is required and overall power consumption and cost of the system are greatly reduced. As a result, the process can be run at high current density without a loss in current efficiency.

It is believed that any excess protons added to the system in an amount greater than that required for the formation of ascorbic acid react with the sulfate ions and form sodium bisulfates which do not cross the cation exchange membrane. Also, any extra sodium bisulfate can transfer a proton to form ascorbic acid.

$$NaHSO_4 + NaAsA \rightarrow AsA + Na_2SO_4 \quad (1)$$

While not wishing to be bound by any particular theory of operation, it is believed that because the $NaHSO_4/Na_2SO_4$ couple also acts to buffer the solution pH the complete conversion of sodium ascorbate to ascorbic acid does not impair current efficiency. As a result, high current efficiency is maintained. Moreover, the $NaHSO_4/Na_2SO_4$ couple acts as a current carrier, thus the cell voltage is not increased by the complete conversion of sodium ascorbate to ascorbic acid.

Another advantage of adding sodium sulfate in the feed stream is the ability to have continuous operation of the salt splitting process with continuous crystallization of ascorbic acid. Sodium ascorbate may be continually added to the feed solution but never be present in solution because it immediately reacts with sodium bisulfate to form ascorbic acid. As such, sodium bisulfate acts as a mediator.

Finally, ion exchange to remove residual ascorbate salts is not required in the present invention with the use of an inorganic salt because the cell is operated at quantitative conversion of ascorbate salt to ascorbic acid.

Alternatively, a stable cation exchange resin may be added to the feed electrolyte solution to provide enhanced conductivity.

Typically the anolyte solution introduced into the anolyte compartment 3 will be an electrochemically inert inorganic acid. Useful representative examples include inorganic acids such as $H_2SO_4$ or $H_3PO_4$, and the anode reaction will be the oxidation of water to produce oxygen and protons (Equation 2).

$$2H_2O \rightarrow O_2 + 4H^+ + 4e^- \quad (2)$$

The catholyte solution, in the three compartment cell embodiment may comprise a base which is added at the time of start-up. Useful representative bases include the hydroxide or carbonate/bicarbonate of the alkali metal ascorbate salt such as sodium hydroxide, potassium hydroxide, sodium carbonate or sodium bicarbonate. Because this method produces a useful product at the cathode, namely base from, e.g., hydroxyl ion and a cation from the ascorbate salt, the introduction of additional new base is usually unnecessary during operation of the cell. The cathode reaction is the production of hydrogen and hydroxyl ions from the reduction of water according to equation 3.

$$2H_2O + 2e^- \rightarrow H_2 + 2OH^- \quad (3)$$

If carbonate/bicarbonate is the preferred product, then gaseous carbon dioxide may be bubbled into the catholyte compartment 5, at a rate sufficient to react with the caustic being formed and to produce the bicarbonate or carbonate salt of the alkali metal cation. If fermentation methods are used to produce precursors of ascorbate, then the carbon dioxide from the fermentation process may be conveniently employed here.

The central compartment 7 is separated from the anolyte compartment 3 and catholyte compartment 5 by a first 9 and second 11 cation exchange membrane. These cation exchange membranes must be stable and there is a choice between strong acid resin containing sulfonic acid groups or weak acid resins containing carboxylic acid groups. The cation exchange membrane may include perfluorinated membranes such as DuPont Nafion® or a non-perfluorinated type. The first cation exchange membrane 9 allows protons from the anolyte compartment 3 to enter the central compartment 7 and react with ascorbate to form ascorbic acid. The proton is bound by the ascorbic acid because it is a weak acid, so therefore the proton is not lost through the second cation exchange membrane 11 to the catholyte compartment 5. Instead, the metal cation which had formed the ascorbate salt is transported across the second cation exchange membrane 11 into the catholyte compartment 5.

In the preferred embodiment, the system temperature should be about 20–50° C. The system may be run continuously with an in-line crystallizer 17 for removal of ascorbic acid product. The crystallizer 17 can preferably be run at a lower temperature than the electrolysis circuit so that the ascorbic acid product, which is less soluble at lower temperatures, will precipitate out in the crystallizer. The depleted feed electrolyte solution will then return to the central compartment 7 for re-saturation with ascorbic acid. Sodium ascorbate may be added to the feed stream at the feed reservoir 13 after the crystallizer 17 in an amount sufficient to replace that being converted to ascorbic acid by electrolysis.

In addition, additional inorganic salts may be added to the feed reservoir, when needed to maintain high conductivity of the cell. In this way, a continuous process may be operated with quantitative conversion of ascorbate salts to ascorbic acid with a consistent high current density.

The salt-splitting of sodium ascorbate to form ascorbic acid in a three compartment cell may be conducted at current densities ranging from 10–1000 mA cm$^{-2}$ and more preferably at 50–300 mA cm$^{-2}$. The solution temperature range should be about 5–80° C. and more preferably 20–50° C. Higher temperatures should be avoided due to decomposition of the product. The process may be run continuously or in a batch mode.

Figure 2:
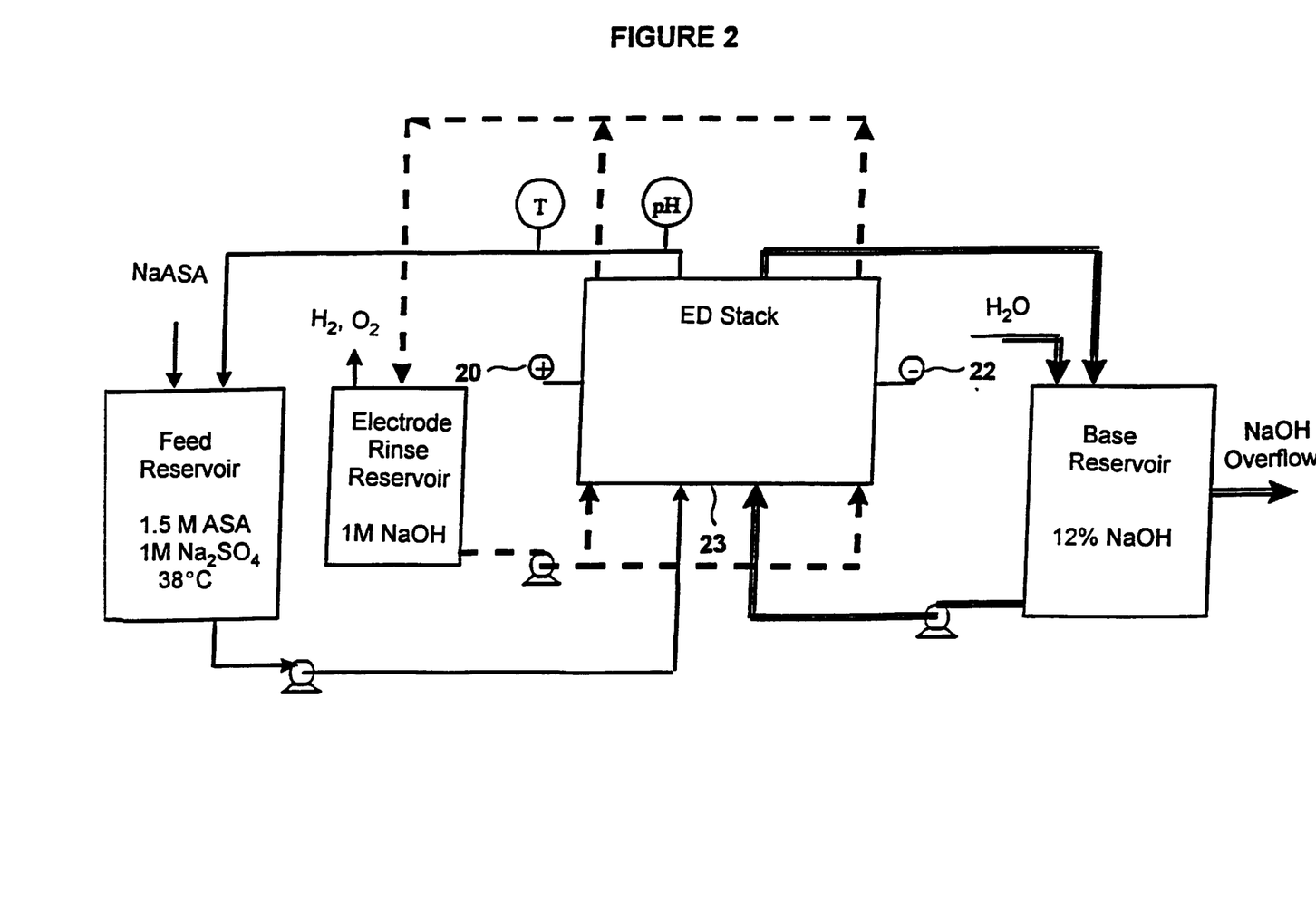
FIG. 2: Diagrammatic View of a Setup for Bipolar Membrane Cell Production of Ascorbic Acid
Figure 3:
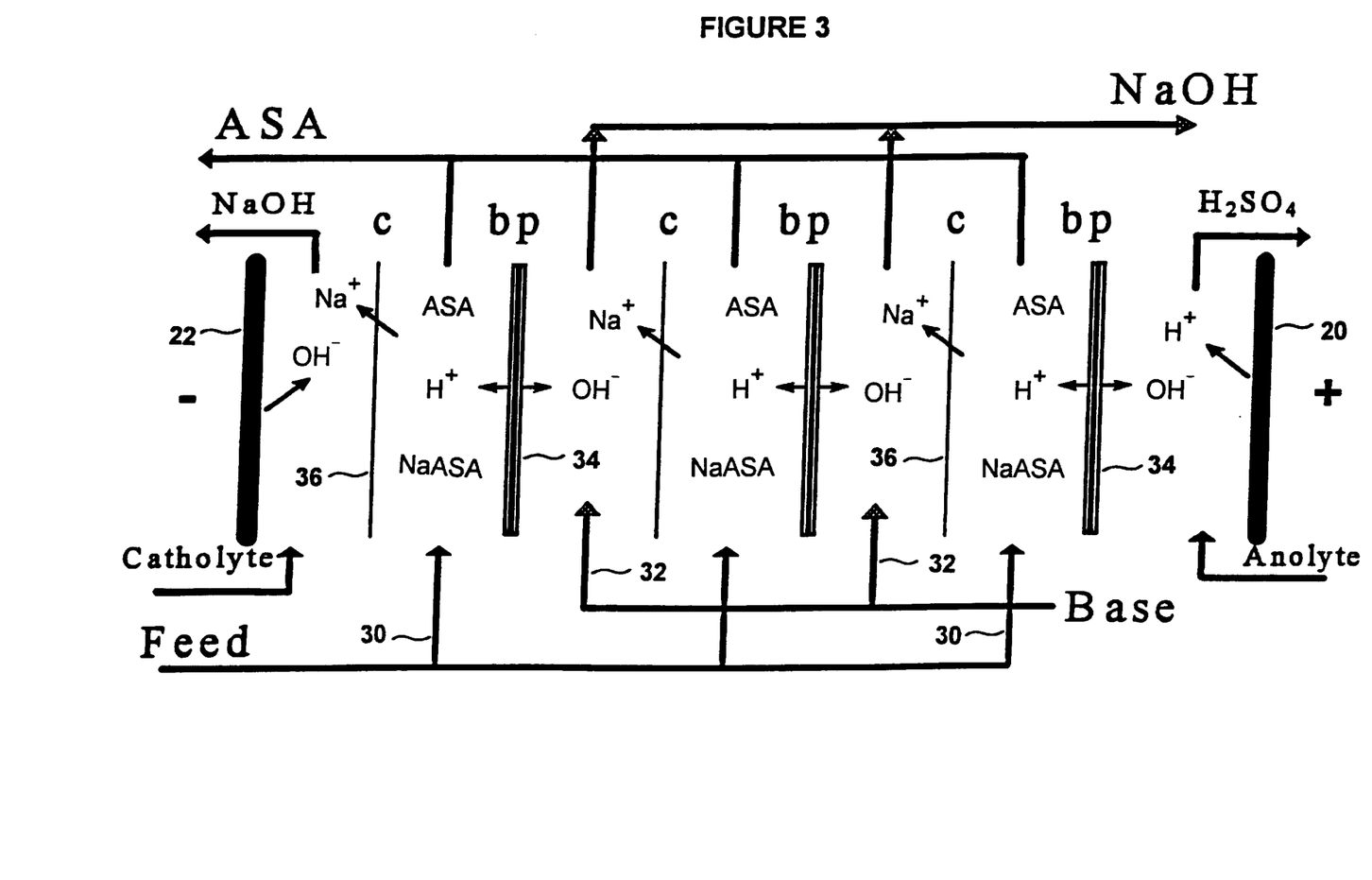
FIG. 3: Enlarged Diagrammatic View of the Bipolar Membrane Electrodialysis Stack shown in FIG. 2 for Aqueous Production of Ascorbic Acid and Sodium Hydroxide

FIG. 2 and 3 depict a diagrammatic view of a setup for bipolar membrane cell production of ascorbic acid. The components of this electrodialysis cell stack comprises an anode 20, rinsed with an anolyte, a cathode 22, rinsed with a catholyte, an electrodialysis cell stack 23 having at least one feed compartment 30 (shown in FIG. 3), at least one base compartment 32 (shown in FIG. 3), disposed between the anode 20 and cathode 22. The anode 20 must be stable to the electrolysis conditions and may include carbons, noble metals or alloys of Pt, Pd, Ir, Au, Ru, etc., noble metals or alloys deposited on a valve metal such as Ti or Ta. The cathode 22 must be stable and may include carbons, noble metals and alloys, nickel, and steels. The anolyte and catholyte, electrolytes used for rinsing the electrodes are typically a solution of strong bases or acids including sodium hydroxide and sulfuric acid.

Introduced into the feed compartment 30 (shown in FIG. 3) is a feed electrolyte solution passing from a feed reservoir 26. The feed electrolyte comprises an ascorbate salt. A wide variety of different ascorbate salts well known in the art may be used. Representative examples of useful ascorbate salts are those which are described in the discussion of FIG. 1. alkali metal salts, such as sodium, potassium, ammonium salts, and preferably sodium ascorbate. The feed electrolyte may be dissolved in any suitable polar solvent. Useful solvents include, but are not limited to water, methanol, short chain alcohols or a mixture thereof. The feed electrolyte solution of the present invention for use during a continuous mode process contains a sufficient amount of ascorbate salt to replace that which is converted to ascorbic acid during the process. In a batch mode process the concentration of ascorbate salt in the feed solution will depend on the polar solvent, temperature and cation used in the process. In general, if the solvent of choice is water then the concentration of ascorbate salt is from about 30 to 70 percent by weight of solution. When methanol is the chosen solvent then the concentration of ascorbate salt is usually less than one (1) percent by weight of solution.

The feed electrolyte solution also contains a sufficient amount of an inorganic salt to improve the conductivity of the solution. Examples of suitable inorganic salts and their advantages are applicable to the bipolar membrane cell and have been described in connection with the above discussion of FIG. 1. As stated above, the inorganic salt improves the conductivity of the solution by introducing additional cations from a source other than ascorbate salts. Because ascorbate salts in the solution are limited to that which are converted to ascorbic acid, the final product of ascorbic acid is free from ascorbate salt contamination which facilitates the formation of fine powder crystals. Additionally, it has been found that a feed solution containing a limited amount of ascorbate salt provides ascorbic acid crystals on a continuous basis. The process can be run continuously and efficiently because the inorganic salt provides sufficient conductivity in the solution while limiting the amount of ascorbate salt to that which is continuously converted to ascorbic acid.

Introduced into the base compartment 27 is a base which is added at the time of start-up. Useful representative bases include the hydroxide or carbonate/bicarbonate of the alkali metal ascorbate salt such as sodium hydroxide, potassium hydroxide, sodium methoxide, sodium carbonate or sodium bicarbonate. Because this method produces a useful product at the cathode, namely base from, e.g., hydroxyl ion and a cation from the ascorbate salt, the introduction of additional new base is usually unnecessary during operation of the cell. The base may be dissolved in any polar solvent. Useful polar solvents include, but are not limited to water, methanol, short chain alcohols or a mixture thereof.

The electrodialysis cell stack 23 further comprising at least one alternating bipolar 34 (shown in FIG. 3) and cation exchange membranes 36 (shown in FIG. 3) separating the feed 30 and base 32 compartments (shown in FIG. 3).

The bipolar membrane 34 (shown in FIG. 3) consists of an anion exchange layer, bonded to a cation exchange. A preferred representative of a bipolar membrane is the Neosepta® BP-1 brand provided by Tokuyama Soda, Japan, in which the anion exchange layer contains resins comprising quaternary amines and the cation exchange layer contains resins comprising sulfonic acid groups. This membrane dissociates water to form a hydroxyl ion and proton at a low potential. Under the influence of the potential field, the protons will move towards the cathode 22 into the feed stream where they combine with the ascorbate ion to form ascorbic acid, displacing the metal cation. The metal cation then migrates across a cation exchange membrane 36 (shown in FIG. 3) into the base compartment 32 (shown in FIG. 3) where it combines with a hydroxyl ion formed at the bipolar membrane 34 (shown in FIG. 3) to produce caustic. As in the three compartment configuration, the cation exchange membrane may be perfluorinated or non-perfluorinated. Many of these two compartment units may be stacked together in a conventional electrodialysis cell with a single pair of electrodes at the outer ends.

If carbonate/bicarbonate is the preferred product instead of caustic, then carbon dioxide may be bubbled into the base compartment 32 (shown in FIG. 3) where it reacts with a hydroxyl ion to form carbonate or bicarbonate. If fermentation methods are used to produce precursors of ascorbate, then the carbon dioxide from the fermentation process may be conveniently employed here.

The bipolar membrane cell process, whether run with aqueous or methanol solutions, may be operated continuously with an in-line crystallizer for removal of solid ascorbic acid product as described above.

The bipolar membrane cell stack may be operated at a current density of about 1–350 mA cm$^{-2}$, and more preferably 10–150 mA cm$^{-2}$. Higher current densities should be avoided due to shorter membrane lifetimes. The unit cell potential drop should preferably not exceed 4 volts, and the temperature range should be between 5–60° C., and preferably 20–50° C. Higher temperatures may damage the bipolar membrane. The process may be run continuously or in a batch mode.

Figure 4:
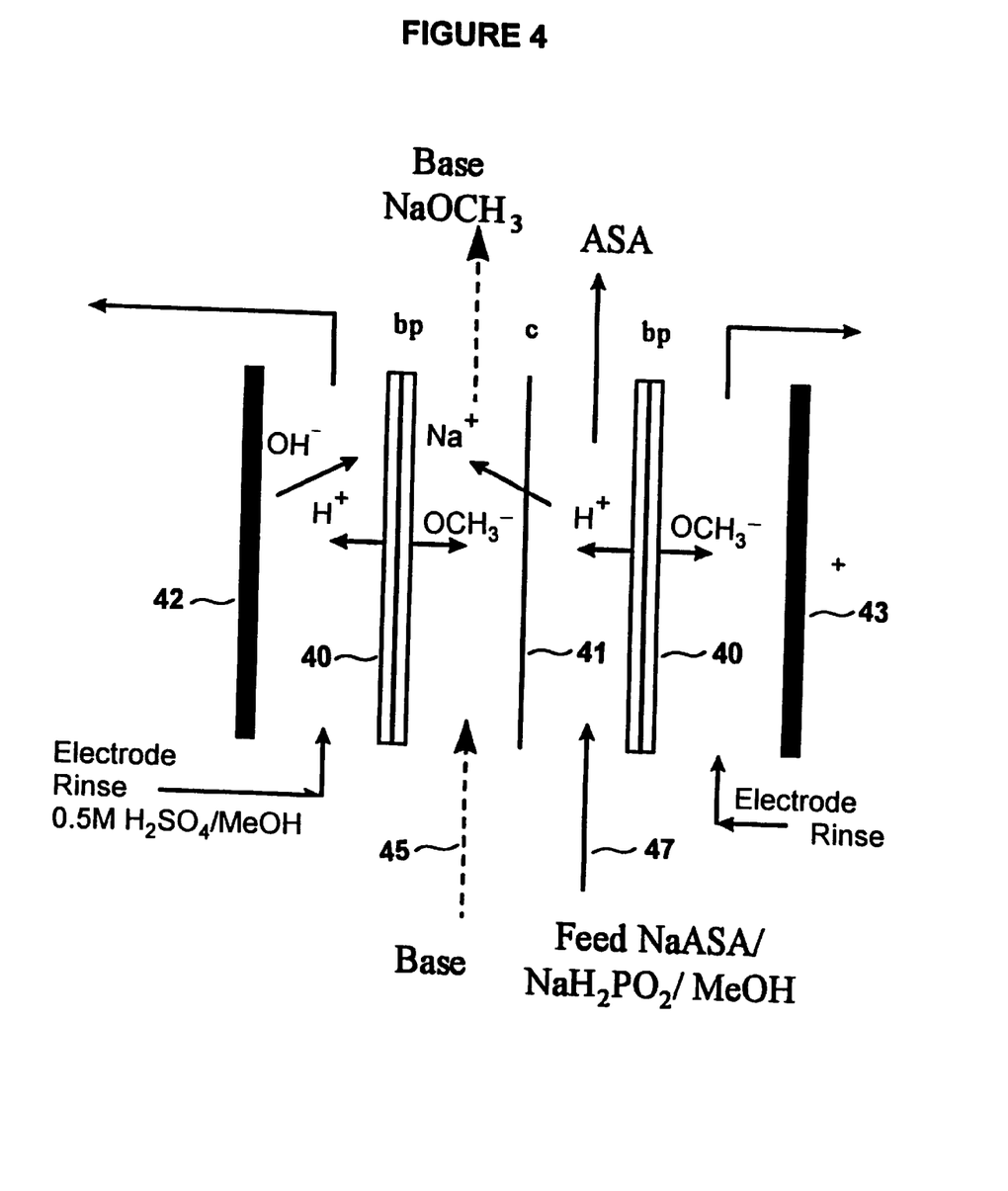
FIG. 4: The Use of Bipolar Membranes for the Production of Ascorbic Acid and Sodium Methoxide in Methanol.

FIG. 4 shows the use of bipolar membranes for the production of ascorbic acid and sodium methoxide in methanol. At least one bipolar membrane 40 may be operated in methanol which is dissociated at the bipolar membrane to form a methoxyl ion and a proton. Thus, the entire system can be non-aqueous. Protons formed at the bipolar membrane 40 will move towards the cathode 42 into the feed stream where they combine with the ascorbate ion to form ascorbic acid in methanol, displacing the metal cation. The metal cation then migrates across a cation exchange membrane 41 into the base compartment 45 where it combines with the methoxyl ion formed at the bipolar membrane to produce sodium methoxide. Introduced into the feed compartment 47 is a feed electrolyte selected from a group consisting of any metal ascorbate salts, including sodium or potassium, or ammonium salts and dissolved in methanol. Also, an inorganic salt is added to the feed solution for the methanol system because of the low solubility of sodium ascorbate in methanol. A soluble source of sodium or other metal is needed for transport across the cation exchange membrane 41 to improve conductivity of the system. Examples of suitable inorganic salts and their advantages have been described in connection with the above discussion of the three compartment cell of FIG. 1. For the production of ascorbic acid and sodium methoxide in methanol, a preferred inorganic salt is sodium hypophosphite.

Figure 5:
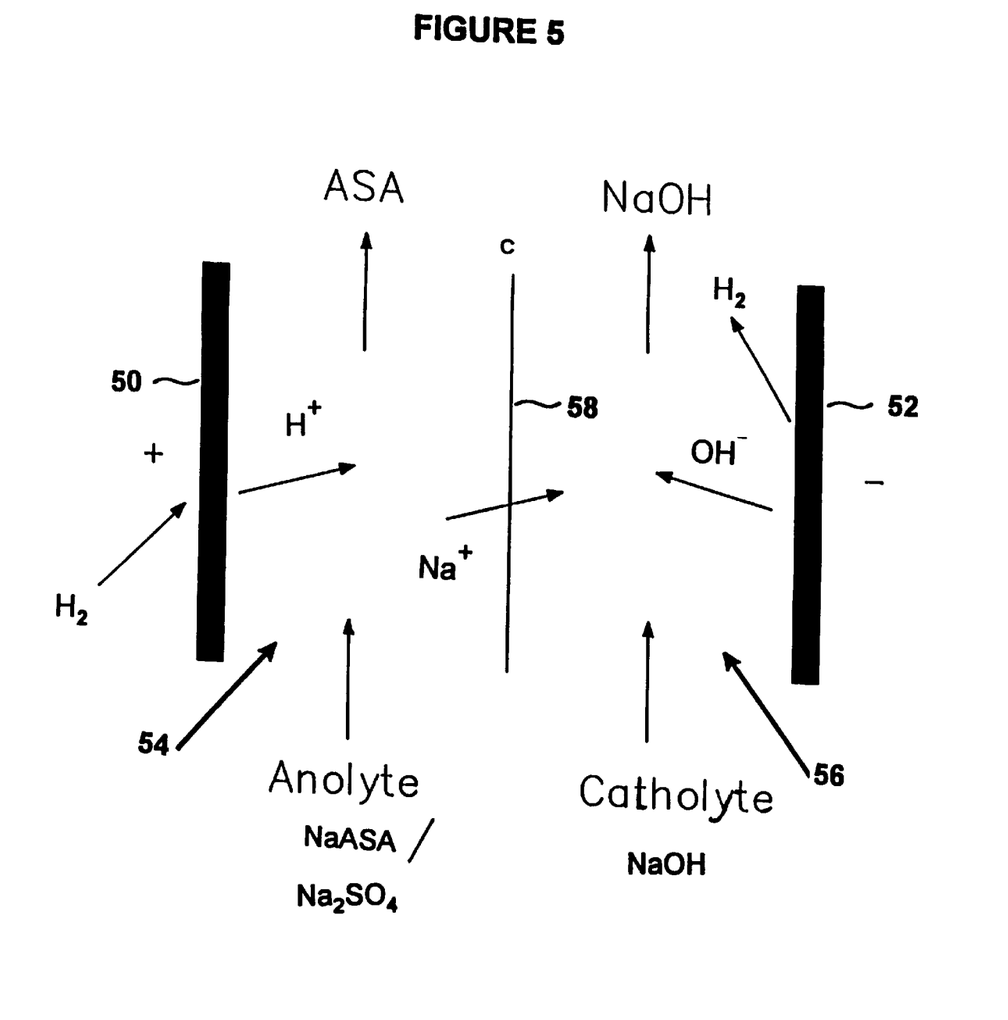
FIG. 5: A Two Compartment Gas Diffusion Anode Cell for the Production of Ascorbic Acid and Sodium Methoxide

FIG. 5 is a representative view of a two compartment gas diffusion anode cell for the production of ascorbic acid and sodium methoxide. This is an alternative to the three compartment cell discussed above. The components of a two compartment cell include an anode 50 in an anolyte compartment 54, a cathode 52 in a catholyte compartment 56, The gas diffusion anode 50 is a hydrogen depolarized anode operating at a potential such that ascorbate or ascorbic acid are not oxidized. Hydrogen gas is supplied to the gas diffusion anode and the anode reaction will be the oxidation of hydrogen to produce protons.

$$H_2 \rightarrow 2H^+ + 2e^- \tag{4}$$

A convenient source of hydrogen is produced at the cathode of the two compartment cell from the electrochemical reduction of water (Equation 3). The gas diffusion anode 50 is a porous electrode structure having a dry side to which hydrogen gas is fed and a wet or anolyte liquor side. Gas diffusion anodes are composed of a corrosion stable, electrically conductive base support generally comprised of a carbon mixed with a non-conductive hydrophobic polymer like Teflon®. The gas diffusion anodes also contain an electrocatalyst for aiding in the electrochemical dissociation of hydrogen. Such catalysts may be composed of highly dispersed metal or alloys of platinum group metal or other material known in the fuel cell art for their ability to catalyze the electrochemical dissociation of hydrogen. The hydrogen depolarized anode may also have porous polymeric layers on the wet side to assist in decreasing electrolyte penetration and fouling. Such porous polymeric layers may be composed of non ionic materials such as Teflon®, PVC, or other ionic type polymers like those formed from polystyrene sulfonic acid or perfluorosulfonic acids.

The cathode 52 must be stable and may include carbons, noble metals and alloys, nickel, and steels.

The anolyte compartment 54 is separated from the catholyte compartment 56 by a cation exchange membrane 58. The cation exchange membrane must be stable and may comprise strong acid resins containing sulfonic acid groups or weak acid resins containing carboxylic acid groups. The cation exchange membrane may include perfluorinated membranes such as DuPont Nafion® or a non-perfluorinated type. The protons formed in the anolyte compartment 54 react with ascorbate to form ascorbic acid. The salt cation displaced from the metal ascorbate salt is transported across the cation exchange membrane 58 into the catholyte compartment 56.

Introduced into the anolyte compartment 54 is the anolyte solution. The anolyte solution comprises an ascorbate salt. A wide variety of different ascorbate salts well known in the art may be used. Representative examples of useful ascorbate salts include, alkali metal salts, such as sodium, potassium, ammonium salts, and preferably sodium ascorbate. The ascorbate salt may be dissolved in any suitable polar solvent. Useful solvents include, but are not limited to water, methanol, short chain alcohols or a mixture thereof. The anolyte solution of the present invention for use during a continuous mode process contains a sufficient amount of ascorbate salt to replace that which is converted to ascorbic acid during the process. In a batch mode process the concentration of ascorbate salt in the feed solution will depend on the polar solvent, temperature and cation. In general, if the solvent of choice is water then the concentration of ascorbate salt is from about 30 to 70 percent by weight of solution. When methanol is the chosen solvent then ascorbate salt is usually less than one (1) percent by weight of solution.

The anolyte solution also contains a sufficient amount of an inorganic salt to improve the conductivity of the solution and facilitate a continuous run of the process. Examples of suitable inorganic salts and their advantages are applicable to the two compartment cell and have been described in connection with the above discussion of the three compartment cell of FIG. 1.

The catholyte solution, in the two compartment cell embodiment may comprise a base which is added at the time of start-up. Useful representative bases include the hydroxide, methoxide, or carbonate/bicarbonate of the alkali metal ascorbate salt such as sodium hydroxide, potassium hydroxide, sodium methoxide, sodium carbonate or sodium bicarbonate. Because this method produces a useful product at the cathode, namely base from, e.g., hydroxyl ion and a cation from the ascorbate salt, the introduction of additional new base is usually unnecessary during operation of the cell.

If carbonate/bicarbonate is the preferred product, then gaseous carbon dioxide may be bubbled into the catholyte compartment 56, at a rate sufficient to react with the caustic being formed and to produce the bicarbonate or carbonate salt of the alkali metal cation.

In this embodiment, the system temperature should be about 5–80° C., and preferably 20–50° C. Higher temperatures may cause degradation of the ascorbic acid product. The system may be run continuously with an in-line crystallizer for removal of ascorbic acid product. The crystallizer can preferably be run at a lower temperature than the electrolysis circuit so that the ascorbic acid product, which is less soluble at lower temperatures, will precipitate out in the crystallizer. The depleted anolyte solution will then return to the anolyte compartment 54 for re-saturation with ascorbic acid. Ascorbate salts and inorganic salts may be added to the anolyte stream in an amount sufficient to replace that being converted to ascorbic acid by electrolysis. In this way, a continuous process may be operated.

The salt-splitting of sodium ascorbate to form ascorbic acid in a two compartment cell may be conducted at current densities ranging from 10–1000 mA cm$^{-2}$ and more preferably at 50–300 mA cm$^{-2}$. The solution temperature range should be about 5–80° C., and more preferably 20–50° C. Higher temperatures should be avoided due to decomposition of the product. The process may be run continuously or in a batch mode.

The invention will be more clearly perceived and better understood from the following specific examples.

EXAMPLE 1

Production of Ascorbic Acid and Sodium Hydroxide in a Three Compartment Cell Crystalline ascorbic acid was made in a three compartment MP Cell (ElectroCell AB, Sweden) having an area of 100 cm$^2$. The cell components were: DSA-O$_2$ anode (ElectroCell AB), planar nickel plate cathode, and Nafion® 350 cation exchange membranes. The electrochemical cell and accompanying setup are shown in FIG. 1. The initial catholyte was a solution of two molar caustic, and the anolyte was three molar sulfuric acid. Water was added to the catholyte to maintain its concentration at about two molar.

The initial feed electrolyte solution was comprised of 2 molar ascorbic acid plus 1 molar sodium sulfate dissolved in water. The experiment was operated at a constant current density of 200 mA cm$^{-2}$ and a temperature of 50° C., and solid sodium ascorbate was added to the feed reservoir at a rate sufficient to replace that which was consumed by the salt splitting electrolysis. The feed electrolyte was held at a pH of 1.0–2.0 by addition of sodium ascorbate. At this pH, most of the ascorbate is present as ascorbic acid.

A slip stream of the feed solution was passed through a crystallizer which consisted of a jacketed glass reservoir with cold (5° C.) water circulating through the jacket and cooling the feed solution in the crystallizer to about 20° C. As the ascorbic acid concentration built up in the feed, ascorbic acid crystals began to precipitate in the crystallizer. The feed solution reached a steady state concentration of about 1.8 molar ascorbic acid.

The experiment was operated for about 5.5 hours. At the end of the experiment, the crystals were removed from the crystallizer and filtered to remove the feed solution. The crystals were then dried in a vacuum oven. 686 g. of dried product was recovered. The product was a white powder which assayed at 96.6% pure and contained 1.3% sulfate. Improved purity could be achieved by better crystallization/filtration/washing techniques and/or recrystallization. The current efficiency for the run was 83%, and the cell voltage across the cell was 8.5–9.0 Volts.

EXAMPLE 2

Production of Ascorbic Acid and Potassium Bicarbonate in a Three Compartment Cell Ascorbic acid and potassium bicarbonate were made in solution in a three compartment MP Cell using the same components and experimental setup as described in Example 1. The initial catholyte was a solution of one molar bicarbonate, and the anolyte was three molar sulfuric acid. The initial feed electrolyte solution was comprised of a solution of 1.5 molar ascorbic acid plus 0.5 molar potassium sulfate. The experiment was operated at a constant current density of 200 mA cm$^{-2}$ and a temperature of 50° C. Solid potassium hydroxide was added to the feed reservoir at a rate sufficient to neutralize the ascorbic acid being formed by the salt splitting electrolysis and maintain the feed electrolyte pH at 1.5–2.0. At this pH, most of the ascorbate is present as ascorbic acid.

The experiment was operated for about 2.5 hours in a batch recycle mode. The bicarbonate concentration in the catholyte compartment increased to 3.5 molar while the ascorbic acid concentration in the feed reservoir was unchanged due to the addition of KOH. The current efficiency for the run was 95%. The voltage drop across the MP Cell was 8.5–9.0 Volts.

EXAMPLE 3

Production of Aqueous Solutions of Ascorbic Acid and Sodium Hydroxide in a Bipolar Membrane Cell Ascorbic acid and sodium hydroxide were produced in a bipolar membrane electrodialysis cell stack. The experimental setup is pictured in FIG. 2. FIG. 3 diagrams the stack itself, showing the transport of ions. The cell components were: Electrosynthesis Co. ED-1-BP cell stack having an electrode area 100 cm$^2$, platinized titanium anode and cathode, Neosepta® BP-1 brand bipolar membranes, and Neosepta® CM-2 brand cation exchange membranes. Three membrane pairs were used. The initial catholyte was a solution of one molar caustic, and the anolyte was one molar sulfuric acid. The initial base was comprised of a solution of 1.5 molar sodium hydroxide. The initial feed solution was comprised of 0.5 molar ascorbic acid plus 1 molar sodium sulfate dissolved in water. The experiment was operated at a constant current density of 100 mA cm$^{-2}$ and a temperature of 40° C., and solid sodium ascorbate was added to the feed reservoir at a rate sufficient to replace that which was consumed by the salt splitting electrolysis. The feed electrolyte was held at a pH of 1.5–2.0 by addition of sodium ascorbate. At this pH, most of the ascorbate is present as ascorbic acid.

The experiment was operated for about 1 hour in a batch recycle mode. The caustic concentration in the base compartment and ascorbic acid concentration in the feed compartment were allowed to build up to about 2.3 and 2.0 molar, respectively, at a current efficiency of 85%. The voltage drop per membrane pair was about 2 Volts.

EXAMPLE 4

Production of Solutions of Ascorbic Acid and Sodium Methoxide in Methanol in a Bipolar Membrane Cell FIG. 4 diagrams the cell stack used for the production of sodium methoxide and ascorbic acid in methanol. The cell components were: ElectroCell AB MicroCell cell stack having an electrode area 10 cm$^2$, graphite anode, platinized titanium cathode, Neosepta® BP-1 bipolar membranes, and Neosepta® CM-2 cation exchange membranes. Two bipolar membranes and one cation exchange membrane were used. The initial catholyte and anolyte were methanol containing 0.5 molar sulfuric acid. The initial base was comprised of a solution of 0.3 molar sodium methoxide, and the initial feed was comprised of a 0.6 molar solution of sodium hypophosphite dissolved in methanol plus 0.075 moles of sodium ascorbate present as a slurry. The experiment was operated at a constant current density of 20 mA cm$^{-2}$ and a temperature of 35–40° C.

The experiment was operated for about 10 hours in a batch recycle mode. The methoxide concentration in the base compartment and ascorbic acid concentration in the feed compartment were allowed to build up to about 0.72 and 0.40 molar, respectively, at a current efficiency of 77%. 74% of the sodium ascorbate was converted to soluble ascorbic acid. The voltage drop per membrane pair was about 15–20 Volts.

EXAMPLE 5

Production of Ascorbic Acid and Sodium Hydroxide in a Two Compartment Gas Diffusion Anode Cell Ascorbic acid and sodium hydroxide are produced in a two compartment MP Cell (ElectroCell AB, Sweden) having an area of 100 cm$^2$ and fitted with a gas diffusion anode. The cell components are: gas diffusion anode (such as those manufactured by E-Tek Corp., Boston, Mass.), planar nickel plate cathode, and Nafion® 350 cation exchange membrane. The electrochemical cell and accompanying setup are shown in FIG. 5. The initial catholyte is a solution of two molar caustic, and the anolyte is a solution comprising 2 molar ascorbic acid plus 1 molar sodium sulfate dissolved in water. Hydrogen gas is supplied to the dry side of the gas diffusion anode.

The experiment is operated at a constant current density of 200 mA cm$^{-2}$ and a temperature of 50° C., and a solid sodium ascorbate is added to the anolyte reservoir at a rate sufficient to replace that which is consumed by the salt splitting electrolysis. Protons formed at the gas diffusion anode combine with ascorbate ion to form ascorbic acid and the liberated sodium ion is transported across the cation exchange membrane where it combines with hydroxide formed at the cathode to produce caustic. The anolyte pH is held at 1.0–2.0 by addition of sodium ascorbate. At this pH, most of the ascorbate is present as ascorbic acid.

EXAMPLE 6

A test was conducted to show the advantages of using sodium sulfate in a salt splitting process which include reduced required cell voltage and increased recovery of ascorbic acid through crystallization. For all runs, the feed pH was held roughly constant by periodic addition of sodium ascorbate to the feed stream. For runs with sodium sulfate present, the pH of the feed was held at about 1.5 so that there was little or no free sodium ascorbate in the system. For runs without sodium sulfate, the system was run at about pH 2 so that roughly 90% of the sodium ascorbate was converted to ascorbic acid. The results were surprising in that the runs having sodium sulfate present showed a large reduction in cell voltage yet exhibited the same current efficiency for the conversion of sodium ascorbate to ascorbic acid. In table 1 the results show that in a three compartment electrochemical cell, the required voltage was surprising reduced to less than half of that required without the addition of sodium sulfate. In the bipolar electrochemical cell the required voltage across the membrane pairs was greatly reduced.

TABLE 1

| Cell | Na2SO4 Added | CD, mA cm-2 | Temp. °C. | NaOH Conc. | NaOH % CE | Cell Voltage | ASA Transport to NaOH (% of ASA Made) |
|---|---|---|---|---|---|---|---|
| 3 Comp. | Yes | 250 | 50 | 2–3 M | 83% | 10–11V | 0.2–0.4% |
| 3 Comp. | No | 250 | 50 | 1–3 M | 85% | 20–30V | 0.2–0.4% |
| Bipolar | Yes | 100 | 40 | 1–2 M | 85% | 2.2 V/pr. | 0.2–0.3% |
| Bipolar | No | 100 | 40 | 1–3 M | 82% | 3.5 V/pr. | 0.2–0.3% |

With the addition of sodium sulfate in the feed stream, the amount of sodium ascorbate introduced into the system can be maintained at a level which is continuously converted to ascorbic acid. Keeping the level of sodium ascorbate to a limited amount, that being no more than that which immediately reacts to form ascorbic acid, increases the ability of ascorbic acid to precipitate out of solution. The results in Table 2 show that the presence of ascorbate salts in solution increases the solubility of ascorbic acid in solution, thereby reducing the overall crystallization yield of ascorbic acid. Furthermore, when ascorbic acid precipitates in the presence of an ascorbate salt, the ascorbic acid forms clumps, and sticks to the glass. By using an inorganic salt in the feed stream essentially all of the ascorbate salt is converted to ascorbic acid and the ascorbic acid precipitates as a fine powder without clumping.

TABLE 2

| NaASA, g | H$_2$O, g | Approx. ASA Solubility at 25° C. | Approx. ASA Solubility at 50° C. |
|---|---|---|---|
| 0 | 25 | 33% | 68% |
| 8.75 | 25 | — | 69% |
| 15 | 25 | 47% | 76% |
| 17.5 | 25 | — | 85% |

Precipitation of ascorbic acid only took a few minutes after cooling from 50 to 25° C. but as the amount of sodium ascorbate increased the time for precipitation increased to several hours. As shown in Table 2, if the amount of sodium ascorbate increases in the feed solution, more ascorbic acid is solubilized in solution thereby preventing the continuous crystallization of product.

We claim:

1. A method for producing ascorbic acid and a co-product base comprising the following steps:
    a) providing an electrochemical cell comprising an anode in an anolyte compartment, a cathode in a catholyte compartment, and a central compartment disposed between the anolyte and catholyte compartments, the central compartment separated from the anolyte and catholyte compartments by a first and second cation exchange membrane;
    b) introducing into the central compartment a feed solution comprising an ascorbate salt and an inorganic salt;
    c) introducing into the anolyte compartment an anolyte comprising an acid;
    d) introducing into the catholyte compartment a catholyte comprising a base;
    e) applying a sufficient voltage across the anode and cathode to convert the ascorbate salt into an ascorbate ion and salt cation, and to form protons at the anode and hydroxyl ions at the cathode wherein the protons migrate through the first cation exchange membrane to the central compartment to combine with the ascorbate ion to form ascorbic acid and the salt cation migrates through the second cation exchange membrane into the catholyte compartment to combine with the hydroxyl ion to form the co-product base.

2. The method according to claim 1 wherein the ascorbate salt is a member selected from the group consisting of sodium ascorbate, potassium ascorbate, lithium ascorbate and ammonium ascorbate.

3. The method according to claim 1 wherein the inorganic salt is a member selected from the group consisting of alkali metal sulfate, alkali metal chloride, alkali metal phosphates and alkali metal bisulfates.

4. The method according to claim 1 wherein the feed electrolyte is continuously introduced into the central compartment.

5. The method according to claim 4 wherein the ascorbic acid is continuously recovered from the central compartment and continuously crystallized.

6. The method according to claim 1 wherein the inorganic salt is sodium sulfate.

7. The method according to claim 1 wherein the co-product base is an alkali metal hydroxide.

8. The method according to claim 7 wherein the co-product base is further treated with gaseous carbon dioxide thereby forming a member selected from the group consisting of alkali metal bicarbonate and alkali metal carbonate.

9. A method for the production of ascorbic acid and a co-product base comprising the following steps:
    a) providing an electrochemical cell comprising an anode, the anode rinsed with an anolyte stream, a cathode, the cathode rinsed with a catholyte stream, and an electrodialysis cell stack disposed between the anode and the cathode, the electrodialysis cell stack comprises at least one feed compartment, at least one base compartment and alternating bipolar and cation exchange membranes disposed between the feed and base compartments;
    b) introducing into the feed compartment a feed electrolyte solution comprising an ascorbate salt and an inorganic salt;
    c) introducing into the base compartment a base electrolyte comprising a base; and d) applying a sufficient voltage across the anode and cathode to convert the ascorbate salt into an ascorbate ion and salt cation, and to form protons and hydroxyl ions at the bipolar membrane, wherein the protons migrate to the feed compartment and combine with the ascorbate ion to form ascorbic acid, the salt cation migrates through the cation exchange membrane into the base compartment to combine with the hydroxyl ions in the base compartment thereby forming the co-product base.

10. The method according to claim 9 wherein the ascorbate salt is a member selected from the group consisting of sodium ascorbate, potassium ascorbate, lithium ascorbate and ammonium ascorbate.

11. The method according to claim 9 wherein the inorganic salt is a member selected from the group consisting of alkali metal sulfate, alkali metal chloride, alkali metal phosphates and alkali metal bisulfate.

12. The method according to claim 9 wherein the inorganic salt is sodium sulfate.

13. The method according to claim 9 wherein the co-product base is sodium hydroxide.

14. The method according to claim 9 wherein the ascorbate salt is continuously introduced into the central compartment.

15. The method according to claim 14 wherein the ascorbic acid is continuously recovered from the central compartment and continuously crystallized.

16. A method for the production of ascorbic acid and co-product methoxide salt comprising the following steps:
   a) providing an electrochemical cell comprising an anode, the anode rinsed with an anolyte stream, a cathode, the cathode rinsed with a catholyte stream, and an electrodialysis cell stack disposed between the anode and the cathode, the electrodialysis cell stack comprises at least one feed compartment, at least one base compartment and alternating bipolar and cation exchange membranes disposed between the feed and base compartments;
   b) introducing into the feed compartment a feed solution comprising an ascorbate salt and an inorganic salt, substantially dissolved in methanol;
   c) introducing into the base compartment a base electrolyte comprising a base; and
   d) applying a sufficient voltage across the anode and cathode to convert the ascorbate salt into an ascorbate ion and salt cation, and to form protons and methoxyl ions at the bipolar membrane, wherein the protons migrate to the feed compartment and combine with the ascorbate ion to form ascorbic acid, the salt cation migrates through the cation exchange membrane into the base compartment to combine with the methoxyl ions in the base compartment thereby forming the co-product methoxide salt.

17. The method according to claim 16 wherein the ascorbate salt is sodium ascorbate.

18. The method according to claim 16 wherein the co-product base is sodium methoxide.

19. The method according to claim 16 wherein the feed electrolyte is continuously introduced into the central compartment.

20. The method according to claim 19 wherein the ascorbic acid is continuously recovered from the central compartment and continuously crystallized.

21. A method to produce ascorbic acid and a co-product base in a two compartment electrochemical cell with a gas diffusion anode comprising the following steps:
   a) providing an electrochemical cell comprising a gas diffusion anode in an anolyte compartment, a cathode in a catholyte compartment, and a cation exchange membrane disposed between the anolyte and catholyte compartments;
   b) introducing into the anolyte compartment an anolyte comprising an ascorbate salt and an inorganic salt;
   c) introducing into the catholyte compartment a catholyte;
   d) introducing into the gas diffusion anode a source of hydrogen gas; and
   e) applying a sufficient voltage across the anode and cathode to convert the ascorbate salt into an ascorbate ion and salt cation, and to form protons at the anode and hydroxyl ions at the cathode wherein the protons, in the anolyte compartment, combine with the ascorbate ion, to form ascorbic acid and the salt cation migrates through the cation exchange membrane into the catholyte compartment to combine with hydroxyl ions thereby forming the co-product base.

22. The method according to claim 21 wherein the feed electrolyte is continuously introduced into the central compartment.

23. The method according to claim 22 wherein the ascorbic acid is continuously recovered from the central compartment and continuously crystallized.

* * * * *